United States Patent [19]

van Andel

[11] Patent Number: Plant 6,048

[45] Date of Patent: Dec. 1, 1987

[54] ALSTROEMERIA NAMED STALSAM

[75] Inventor: Jacob van Andel, Aalsmeer, Netherlands

[73] Assignee: Van Staaveren B.V., Aalsmeer, Netherlands

[21] Appl. No.: 806,264

[22] Filed: Dec. 6, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new variety of Alstroemeria plant characterized by its medium sized blooms, the lower petals of which are distinguished by an attractive combination of Azalea Pink, Jasper Red and Rose Bengal coloration which contrasts nicely with the smaller upper petals which are mainly of a Yellow coloration in the central petal area with the end portions of the petals being of a Jasper Red color, these upper petals all being marked with short, brown pencil stripes which spread outwardly from the base of the petal to almost the petal tips. This plant is further distinguished by its strong, vigorous, upright growth habit with the main stems or canes reaching a height of about 160 cm. and the flowers being produced profusely and continuously the year around.

1 Drawing Figure

BACKGROUND OF THE NEW PLANT

This Alstroemeria hybrid originated as a seedling resulting from my crossing of plants selected from individually identified members of my breeding stock maintained at Aalsmeer, The Netherlands, for developmental purposes, this particular seedling having been selected by me for propagation and test because of the overall Pink, Red and Yellow coloration of its blossoms, which appeared to be produced profusely on strong, upright, umbel stems. This new plant is the result of breeding efforts carried on by me at Aalsmeer, The Netherlands, since 1981 with the object of producing new types of Alstroemeria plants and the selected seedling was propagated by me and under my direction by root division through several successive generations which clearly demonstrated that the distinctive and novel characteristics of the parent plant would hold true from generation to generation and appeared to be firmly fixed.

DESCRIPTION OF THE DRAWING

This new variety of Alstroemeria plant is illustrated by the accompanying photographic drawing which, in full color, shows the flowers of a blooming umbel of the plant and demonstrates the unique and distinctive coloration and form of the flowers, the color rendition being as nearly true as it is possible to obtain by conventional photographic procedures.

DESCRIPTION OF THE NEW PLANT

The following is a detailed description of my new Alstroemeria plant with color designations according to The R.H.S. Colour Chart of The Royal Horticultural Society of London, England.

THE PLANT

Origin: Seedling.

Parentage:

*Seed parent.*—Breeding Stock Plant No. 7117-1 (unpatented).

*Pollen parent.*—Breeding Stock Plant No. 9318-1 (unpatented).

Classification:

*Botanic.*—Alstroemeria hybrid.

*Commercial.*—Alstroemeria.

Form: Erect bush.

Height: About 160 cm.

Main Stem:

*Height.*—About 160 cm. with flower bearing branches in simple umbel arrangement at its top.

Growth: Strong, vigorous and upright.

Root stock: Tuberous.

Foliage:

*Quantity.*—Abundant.

*Number of leaves.*—Various, depending upon season.

*Size of leaf.*—Various, depending upon season.

*Leaf shape.*—Elliptic with entire margins.

*Texture.*—Leathery.

*Color.*—Upper side — Dark Green. Under side — Grey Green.

Rhizomes:

*Color.*—White.

*Size.*—Various, depending upon season.

THE BUD

Form: Pear shaped.

Size:

*Diameter.*—About 20 mm.

*Length.*—About 45 mm.

Calyx: This plant has no calyx, the six petals of the flower being perianth and dividing simultaneously.

Peduncle:

*Length.*—About 50 mm.

*Color.*—Middle Green.

*Character.*—The penducle is sturdy and extends upwardly at an angle of about 30° from the flowering stem.

THE FLOWER

Blooming habit: Continuous and profusely the year around.

Flower size: Medium.
*Diameter.*—About 50 mm.
*Depth.*—About 50 mm.
Borne: Singly.
Shape: Funnel-like with petal tips tending to curl outwardly.
Petalage:
*Number of petals.*—Six.
*Arrangement.*—Two concentric circles of three petals each.
*Form.*—Obovate.
*Texture.*—Leathery.
*Appearance.*—Shiny.
*Color.*—Outer petals — Mainly 38A with a wash of 39B toward the base and with wide margins of 57D. Upper petals — Main body 13A/B with petal tips of about 39B. All of the upper petals have numerous short pencil stripes extending outwardly from the base to almost the tips.
Peduncle or flower stem:
*Length.*—About 50 mm.
*Color.*—Middle Green.
Persistence: The flowers hang on and dry.
Lasting quality:
*On plant.*—About 15 to 20 days.

*As a cut flower.*—About 10 days.

REPRODUCTIVE ORGANS

Stamens:
*Number.*—Six, there being one opposite each petal.
Anthers:
*Color.*—Grey/Green.
Filaments:
*Color.*—Salmon.
Pistils:
*Number.*—One.
*Color.*—Purple/Pink.
Stigma:
*Color.*—Light Orange.

THE FRUIT

Fertility: The fruit is fertile. Shape: Capsular.
Color at maturity: Light Brown.

I claim:

1. The new and distinctive Alstroemeria plant, substantially as herein shown and described, distinguished by its unique color combination of its large lower petals and the contrasting coloring and the short pencil stripes spread over the length of its upper petals.

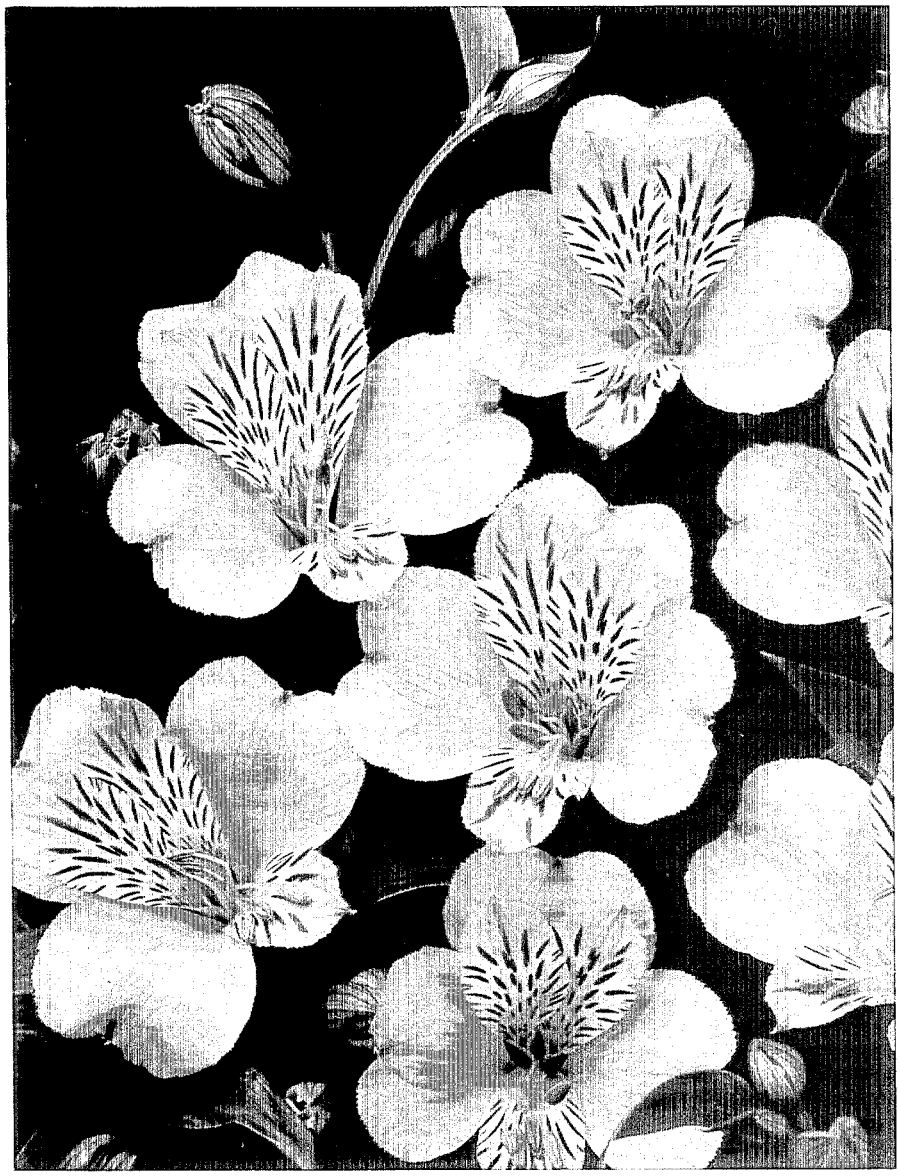

* * * * *